United States Patent [19]

Nevyas et al.

[11] 4,355,871
[45] Oct. 26, 1982

[54] KERATOMETER

[75] Inventors: Herbert J. Nevyas, Narberth, Pa.; Alan C. Traub, Framingham, Mass.

[73] Assignee: Diversitronics, Inc., Broomall, Pa.

[21] Appl. No.: 168,813

[22] Filed: Jul. 14, 1980

[51] Int. Cl.³ .............................................. A61B 3/10
[52] U.S. Cl. ..................................... 351/13; 356/376; 356/390
[58] Field of Search ....................... 351/13, 40; 350/30; 356/124, 125, 127, 376, 390

[56] References Cited

U.S. PATENT DOCUMENTS

| | | | |
|---|---|---|---|
| 3,248,162 | 4/1966 | Knoll | 351/13 |
| 3,264,932 | 8/1966 | Hendricks | |
| 3,288,021 | 11/1966 | Hopkins | |
| 3,482,904 | 12/1969 | Volk | 351/13 |
| 3,969,019 | 7/1976 | Nohda | 351/13 |
| 4,046,463 | 9/1977 | La Russa et al. | 351/13 |
| 4,157,859 | 6/1979 | Terry | 351/13 |
| 4,172,639 | 10/1979 | Lang et al. | 351/13 |

Primary Examiner—R. A. Rosenberger
Attorney, Agent, or Firm—Seidel, Gonda, Goldhammer & Panitch

[57] ABSTRACT

In an optical beam-doubling and image-rotating device, beam splitting means are provided for creating a first and a second image of an optical target in conjunction with means for rotating the light-ray family associated with the second image yielding a second image which has been rotated axially through a defined angle with respect to the first image, in further conjunction with additional beam splitting means so disposed as to combine the first and rotated second images so that they may be visually compared under the conditions of a specifically defined relative angular displacement. The disclosed use is in measuring the sphericity of the cornea of the eye during ophthalmic surgery.

34 Claims, 10 Drawing Figures

KERATOMETER

BACKGROUND OF THE INVENTION

This invention applies to the art of ophthalmic surgery and particularly to microsurgical procedures which involve the suturing of the corneal surface in the eye of the patient while the surgeon observes the procedure through a microscope.

More particularly, the invention teaches an improved means whereby the ophthalmic surgeon may adjust the relative tensions in the various sutures so as to ensure that the corneal surface will assume a perfectly spherical configuration in order to avoid a condition of astigmatism in the optical system of the eye.

The vertebrate eye, which includes the human eye, is a critically structured biological mechanism which can function properly only if each of its separate mechanisms is in proper function. One such mechanism is the ocular optical system which ensures that a proper image of a target field will be formed on the retina. The optical system itself includes several image-forming elements, among which is the eye lens located behind the iris diaphragm and its pupil. An important part of the optical system is the cornea, a curved, horny membrane which serves as a transparent skin over the center of the eye. The cornea serves to contain the ocular fluids, which have a higher refractive index than the air external to the cornea. It thus serves as a refractive element which complements the image-forming capabilities of the eye lens.

In an optimally functioning eye, the lens and cornea are rotationally (or "axially") symmetrical about the optical axis, implying that if the lens or cornea were to be rotated about this axis, no change would result in the optical nature of the retinal image.

It is a common defect in the human eye for one or the other of these elements to exhibit departures from axial symmetry to a greater or lesser extent. The most common such departure is one in which one or more of the lenticular or corneal surfaces assumes an elliptical configuration instead of the spherical curvature of the normal surfaces. In such cases, the eye suffers to a greater or lesser degree from the commonly known defect of astigmatism. With this defect, the subject experiences the visual anomaly of seeing vertical lines, for example, to be in sharper focus than horizontal lines or vice versa. Alternatively, lines at any arbitrary inclination may appear sharply focused whereas lines at a 90° inclination to said lines appear relatively unfocused, depending upon the angular orientation of the astigmatic axes. Astigmatism occurs as a result of the ocular optical system exhibiting a different focal length along one diametrical plane than along the orthogonal plane inclined at 90° to it. Most often, astigmatism in a patient may be corrected by use of prescribed eyeglasses which incorporate a counter-balancing astigmatism of the proper angular orientation and refractive power.

There are certain surgical procedures which involve the replacement of or repairs to the corneal surface. Such procedures are performed in connection with cataract removal or with corneal transplants or repairs because of damaged or injured tissue or various other causes. In these procedures, it is highly desirable that the restored cornea be as spherical as possible in order to minimize any astigmatic effects.

In order to ensure sphericity, the ophthalmic surgeon has had access to several commercially available optical devices which serve as aids during the surgical procedure. In general, such devices make use of the reflective properties of the cornea in which the latter is made to serve as a partial mirror.

Most often, the method used is to project an image of a perfect circle onto the cornea such that the center of the circle is aligned with the ocular axis. By visual inspection, the surgeon may determine whether the image of the circle, as reflected in the cornea, is perfectly circular. If not, then a non-spherical condition is indicated which may be remedied by adjustment of the proper sutures. Through his professional skills and proficiency, the ophthalmic surgeon is able to determine which sutures must be adjusted in order to correct the non-spherical condition.

Corneal surgical procedures involve relatively small physical dimensions and thereby require close visual inspection by the practitioner. To this end, the procedure is most often performed by observation through an ophthalmic microscope. When such microscopes are equipped with the aforesaid sphericity-correction aids, such aids are prepared in the form of self-contained illuminated optical targets, e.g., circles. These targets, when properly positioned over the eye of the patient, allow the surgeon to carry out the aforedescribed function of recognizing departures from sphericity.

In some cases, the surgical microscope system is provided with various devices to aid in a more acute assessment of such departures than can be performed by the unaided eye of the observer. Such devices may include reticles, or measuring scales, which are incorporated into the microscope system. Alternatively, they may incorporate beamsplitting or image-doubling devices which provide a primary image of the reflected pattern in conjunction with a secondary or "ghost" image of the reflected pattern. By optical means, the secondary image is moved with respect to the primary image. Through manipulation of various knobs and controls, the surgeon is able to compare the physical dimensions of the separate images in order to recognize any departure from circularity.

It is a feature of the prior art that such measurements require the manipulation of various mechanical controls. This manipulation is distracting and tedious to the surgeon whose full attention and manual capabilities are required to be directed at surgical manipulations on the patient.

An important teaching of the present invention is a means of providing the surgeon with a sensitive and convenient method of determining the degree of departure from perfect circularity of a reflected image of a target circle or of other geometric forms, while requiring a minimal amount of attention or of manipulative activity.

It is a further teaching of this invention that the described measurement means may be applied to other human endeavors in which certain geometrical properties of various visual targets must be assessed.

The preferred embodiment of this invention is directed toward the ophthalmic surgical application. In particular, it is directed to the problem of measuring the degree of sphericity or, contrariwise, of ellipticity, in the human cornea. Traditionally, instruments for performing measurements upon the cornea have been named keratometers and fall under the practice of keratometry. It is in this sense that the present invention is described as a keratometer, but it is to be understood that in the sense of the invention, the application of the concept is not intended to be limited to the practice of keratometry.

SUMMARY OF THE INVENTION

A beamsplitter is provided within the body of a microscope eyepiece. The plane of the beamsplitter is disposed at a 45° angle to the optical axis of the microscope. The beamsplitter serves to deflect, through a 90° angle, a predetermined portion of image-forming light rays proceeding from the object being observed, the target, via the microscope. The remaining portion of the light rays continues uninterrupted.

A deflected or secondary ray family is further redirected by a full mirror (in contradistinction to a partial mirror or beamsplitter) which is oriented parallel to the beamsplitter. The full mirror deflects the secondary rays through a second 90° angle in such manner that the secondary and the undeviated primary ray families are parallel and are proceeding in the same direction although now displaced in side-by-side relationship.

The secondary ray family is made to traverse an optical image rotating device, such as a dove prism, which has the capability of rotating the image-forming rays about their own propagation axis through any desired angle, depending upon the angular orientation of the image rotating device about its own optical axis. The angular deviation of the image-rotating device is preferably adjusted to 90° so that the final secondary image will be perceived as being perpendicular to the final image as formed by the primary rays.

Upon leaving the image rotator, the secondary ray family is again caused to be deflected through a 90° angle to its axis by use of a second full mirror mounted at 45° to the optical path. The direction of deflection is toward the primary ray axis so that the secondary and primary ray axes will intersect. At the point of intersection is a second beamsplitter which is oriented parallel to the second full mirror. According to conventional optical terminology, we use the term "beamsplitter" in referring to the second beamsplitter because its optical properties are identical to those of the first beamsplitter. It is to be understood, however, that the function of the second beamsplitter is to combine the first and second light-ray beams. In this case, the beamsplitter is more aptly termed a "beam combiner" although this term is rarely used in optical parlance.

At the second beamsplitter, a portion of the secondary rays is again deflected through a 90° angle into the direction of the eye of the observer. The remaining rays pass through the beamsplitter and serve no immediate purpose.

Also at the beamsplitter, a portion of the primary rays is transmitted in its original direction so as to join and to become coincident with the reflected portion of the secondary rays. The remainder of the primary rays is reflected by the beamsplitter through a 90° deviation and serves no immediate purpose.

Both ray families continue through the lens element or elements of the microscope eyepiece system where they are focused in the usual manner to provide to the observer a magnified image of the target.

In the invention, the magnified image consists of a double image of the target comprising a primary and a secondary image in which the secondary image is presented at right angles to the primary image, having been rotated through a 90° angle. The axis of rotation coincides with the optical axis of the microscope.

For the purpose of illustrating the invention, there is shown in the drawings a form which is presently preferred, it being understood, however, that this invention is not limited to the precise arrangements and instrumentalities shown.

DETAILED DESCRIPTION OF THE INVENTION

Figures 1, 2:
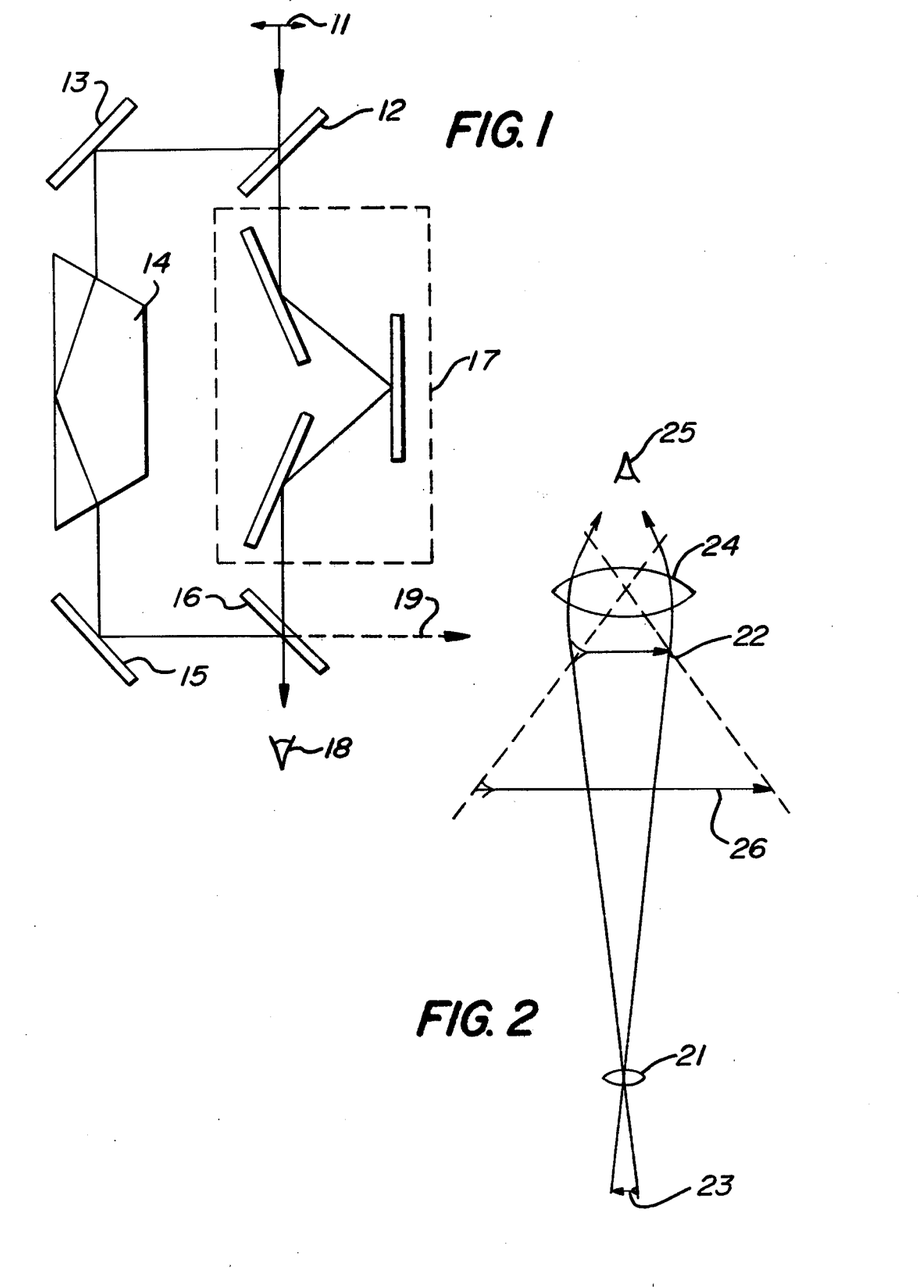
FIG. 1 is an optical schematic diagram of the invention.
FIG. 2 is a diagrammatical view representing the optical system of a typical microscope and is presented for purposes of clarification of the invention.

The invention is best understood by reference to FIG. 1 which shows a preferred embodiment. In turn, the meaning of FIG. 1 is clarified by reference to FIG. 2.

FIG. 2 shows the optical system of a basic microscope in which an objective lens 21 forms a magnified primary image 22 of a target 23 which, in this case, is understood to be the cornea of a patient's eye. The primary image 22 is formed in space by the convergence of focused light rays and is available for further magnification by an eyepiece or ocular 24. The ocular serves as a magnifying lens so that the observer, whose eye 25 is located as shown, will observe a greatly magnified image 26 of the target 23.

The foregoing serves to illustrate the fundamental optical principle of any microscope.

We consider, now, the case where the principal object of visual interest in the patient's cornea is the reflected image of a luminous ring of light, which luminous ring originated in a special illumination source which, by one or another of several possible means, is configured and is affixed to the microscope in the vicinity of and concentric with the objective lens 21.

In such a case, according to the fundamentals of microscope operation, an enlarged image of the reflected luminous ring will appear in the plane of the primary microscope image 22 and will thus be available for further magnification by the ocular 24 so as to be perceived as a further magnified, secondary microscope image 26 by the eye of the observer 25.

In the event that the corneal surface 23 is perfectly spherical, the observer will perceive a circular image which represents a magnified view of the corneal reflection of the original luminous ring. If the corneal curvature departs from sphericity and, instead, includes an elliptical component, the observer will perceive an image which is to a greater or lesser extent elliptical, depending upon the degree to which the corneal curvature departs from sphericity.

The foregoing discussion illustrates the basic principle of keratometric sphericity measurement, in which the nature of the curvature of a patient's cornea may be assessed in terms of the perceived view, via a microscope, of the reflected image of a luminous ring or other target.

In cases where the corneal curvature departs substantially from a truly spherical form, the presence of ellipticity in the secondary image 26 is readily detectable. In situations where the departure from sphericity is minimal, the observer has difficulty in recognizing the associated minimal degree of ellipticity in the secondary image 26.

It is the purpose of the present invention to provide an increased degree of recognition, by the observer, of minimal departures from circularity in the secondary image 26. We thereby achieve a measurement method which is highly sensitive to curvature deviations of the cornea and thus allow the ophthalmic surgeon to perform suturing procedures which result in a high degree of correction of residual corneal-curvature imperfections.

In the schematic diagram of the invention, as shown in FIG. 1, there is a luminous target 11. It is to be understood that target 11 corresponds to the magnified primary image 22 of FIG. 2 which is an aerial image which exists in space and which could be visually perceived if a ground-glass screen or other diffusing sheet were to be placed in its plane. The luminous target 11 serves as the starting point in our description of the invention and should be thought of as a magnified, luminous ring of either perfect or imperfect circularity, and whose degree of circular perfection is to be determined by the means taught in this invention.

The method of the invention may now be made clear. The method is addressed to the question of how best to determine the degree of circularity of a nearly circular object. In our method, we teach a means of readily forming a double image of said object and of rotating one of the images 90° with respect to the other, and of then recombining the images so as to provide a convenient and reliable reference figure whereby any departure from circularity may be readily perceived.

As an example, we cite the hypothetical case wherein the object under inspection is indeed a perfect circle. In such a case, the procedure of doubling, selectively rotating, and recombining the images would result in complete registration and therefore a composite image of a perfect circle. However, in a situation where the inspected object exhibited a slight degree of ellipticity, the recombined images would not show perfect registration. Instead, a small amount of ellipticity would be clearly recognizable by virtue of overhanging parts of the elliptical images where they were not in perfect registration.

In FIG. 1, light rays from the target 11 proceed to a beamsplitter 12 where they are partly reflected and partly transmitted by virtue of the beamsplitter action which will be explained presently. The beamsplitter is disposed at an angle of 45° to the optical axis of the rays and hence causes the reflected portion to be deflected through a 90° angle. Said reflected and deflected portion is then intercepted by a full mirror 13, preferably of the first-surface type, which is disposed parallel to beamsplitter 12.

The term "full mirror" is used to signify a mirror which is essentially fully reflecting except for some nominal reflectance loss due to absorption in the reflecting medium. Full mirrors are to be distinguished from partial mirrors, of the beamsplitting type, which are frequently referred to in this discussion.

First-surface mirrors are those in which the reflecting surface exists on an exposed surface of a supporting member such as a sheet of glass. Such a mirror exhibits the desirable properties of being more highly reflecting and therefore more optically efficient that its second-surface counterparts in which the reflecting surface is prepared at the rear surface of the supporting member. Second-surface mirrors are typified by ordinary mirrors in common use in domestic, automotive and other applications.

A further advantage in the use of a first-surface mirror is that its reflected components are free of undesirable "ghost" components. Such components arise in the case of second-surface mirrors from unwanted reflections occurring at the forwardmost reflective surface of the supporting member.

The desirability of using first-surface mirrors in precision optical instruments is well appreciated by practitioners of the optical instrumentation art.

Upon reflection by mirror 13, the light rays undergo a second 90° deflection so that they are now propagating parallel to the light ray family which has been transmitted by beamsplitter 12. They are then caused to enter an optical image rotation device, which is shown in FIG. 1 as dove prism 14. A dove prism is indicated here as a preferred choice from among several known optical image rotation devices whose actions will be explained subsequently.

Upon leaving the optical image rotation device 14, the light ray family is intercepted by another full mirror 15, also preferably of the first-surface type, which is disposed parallel to beamsplitter 16. The mirror 15 causes the light rays to undergo a third deflection so that they are propagating toward the primary optical path and will intersect said path at the second beamsplitter 16.

Referring now to the first beamsplitter 12, the transmitted rays are caused to undergo a detour, via an optical device 17, which we refer to as a path lengthener. The purpose of the detour is to ensure that the primary light rays, which are transmitted by beamsplitter 12, will have traveled an optical path distance equal to that which is traveled by the secondary rays, which had been reflected by first beamsplitter 12, by the time the two ray families are subsequently joined, which joining is to be effected by second beamsplitter 16. Were the optical distances not to be equal, the subsequent focusing action of the microscope eyepiece lens system would achieve the undesirable effect of placing the two focused images of target 11, as seen by the observer, at different distances along the optical system axis. The purpose of path-length equalization is to ensure that the primary and the rotated secondary images will be in focus in the same plane. Otherwise, the observer would perceive one of the images to be in sharp focus while the other was not.

Upon leaving path lengthener 17, the primary light rays resume their original direction of propagation and shortly arrive at the second beamsplitter 16.

It will be seen that the primary and secondary light ray families which have traveled separated pathways through the optical system are now under such circumstances as to be rejoinable at their intersection. The rejoining is carried out by the secondary beamsplitter 16 whose plane is so oriented as to bisect the 90° angle of intersection of the primary and secondary rays.

At beamsplitter 16, a predetermined portion of light-ray intensity of the secondary rays will be deflected through a 90° angle into the direction of travel of the primary light-ray family. The remaining portion will be transmitted and will serve no useful purpose in this portion of the description of the invention.

Also at beamsplitter 16, a predetermined portion of the light-ray intensity of the primary rays will be transmitted where they will join the reflected rays of the secondary ray family. The remaining portion will be deflected by beamsplitter 16 at an angle of 90° to the original propagation direction and again, for purposes of the immediate description, will achieve no useful purpose.

It should be indicated, however, that those portions of the light-ray families which are deemed in this immediate description to serve no useful purpose, which have been designated 19, may nonetheless be made to serve other purposes. As an example, we cite the possibility of placement of a second microscope ocular in such position as to intercept the otherwise lost ray families, thus to permit a second observer to witness essentially the same optical phenomena which are witnessed by the first observer. Alternatively, a photographic camera, television camera or other optical image sensing device may be adapted in such position as to make use of the otherwise lost light ray family for purposes of separate documentation or display, such as for photographic recording purposes or for medical classroom teaching purposes.

Having been recombined, the primary and secondary light ray families will then proceed on their normal course through the ocular optical system where they are rendered as useful visible images at the eye 18 of the observer.

We refer now to the natures of the beamsplitters which are indicated as elements 12 and 16 and to the manner in which they are able to divide and to recombine light rays. Beamsplitters are well known to practitioners of the optical arts and may be considered as partial mirrors, being partly reflecting and partly transmitting. In one common form, they are prepared upon a substrate of smooth, transparent optical material such as glass. Alternatively, a beamsplitter may be prepared upon a thin plastic membrane. The simplest form of beamsplitter would be a thin sheet of untreated glass wherein ordinary reflection by the two glass/air surfaces is effective in reflecting a portion of incident radiation and in transmitting the remainder. The ratio of reflected radiation to incident radiation is a function of the refractive index of the reflecting material and of the angle of incidence at which the light rays impinge upon the surface. For ordinary glass upon which the light rays impinge perpendicularly, the total reflected component is approximately eight percent. The ratio increases with steeper angles of incidence and reaches approximately twenty percent at 45°. As the angle approaches 90°, or "grazing incidence", the reflected components approach 100 percent in reflected intensity.

In ordinary use, both the front and rear surfaces of the glass serve to reflect the ray families. When the families are subsequently used to form images, and if the front and rear reflecting surfaces are appreciably separated from each other, there is the undesirable possibility of double-image formation in which two images of the same object are perceived with the images being slightly displaced with respect to each other in their plane of formation. For this reason, in using glass or other transparent materials as beamsplitters without the addition of other materials, it is desirable for the beamsplitting sheet to be as thin as possible. Plastic membranes, otherwise known as pellicle beamsplitters, are often used for this purpose.

In many applications, beamsplitters are used at a 45° orientation to the incident rays so as to deflect them through a 90° angle. Often, the inherent reflectivity of glass or of other uncoated substrates is insufficient to reflect the desired portion of the incident rays. In such cases, various methods are known by which the reflectivity of the beamsplitter may be enhanced. A common means is to provide either a chemically deposited or a vacuum-deposited metallic coating on one of the surfaces, of such thickness as to be partly reflecting and partly transmitting in the desired amounts. However, it is a property of metals that they are absorptive of light passing through them and so it will be inevitable that a portion of the incident radiant power will be lost in the metallic layer.

Various metals may be used for this purpose, e.g., aluminum, silver and inconel. In many cases, the metal is applied in such thickness that the final product will divide the incident radiant power into three approximately equal portions, each being reflected, transmitted or absorbed.

It is a property of some metals that they are spectrally selective in their absorption processes, with the result being that a metallic beamsplitter will preferentially transmit a higher proportion of light of a given color than of another color, resulting in a slightly colored transmitted image which may or may not be desirable. Simultaneously, the reflected portion of the light rays may take on a slight complementary hue. Examples of this are metallized-silver beamsplitters which transmit slightly bluish images when exposed to white light, and metallized-gold beamsplitters whose transmitted images are to some extent green.

Metallic and other beamsplitters, to be described, are often protected against abrasion and other destructive influences via a transparent cover plate which is cemented to the prepared surface. In cases where reflections from the outer surfaces of the cover plate and of the substrate may be objectionable, these reflections may be reduced in intensity by use of chemically or vacuum-deposited antireflection coatings which are well-known to those skilled in the optical sciences.

It often happens that the absorption loss which occurs in metallic layers is not tolerable in a given optical use of a beamsplitter. In such a case, the well known use of dielectric (non-absorbing) interference films is resorted to. Such films, microscopic in thickness, have the property of altering the reflective properties of an optical substrate. They may be used in single layers or as multiple layers of separate, vacuum-deposited materials, depending upon the degree of reflectance enhancement which is desired. The degree of reflectivity is determined by the refractive index values of the materials being used, by the number of layers of film material, by the wavelength of the light being reflected, and by the angle of incidence of the impinging light. Such films are designed beforehand according to the well-known laws of optics and the design considerations are well documented in optical technical literature. The optical thicknesses of the individual layers are a multiple of a quarter wavelength of light for whatever wavelength and angle of incidence are of interest, and so the multilayer coating cannot be effective for all wavelengths and angles simultaneously. However, these coatings can be made reasonably effective over some broad, if limited, wavelength region such as the visible spectrum, even though the effectiveness is reduced in the adjoining ultraviolet and infrared spectral regions.

Another form of beamsplitter is known to optical practitioners as the "prism" or "cube" beamsplitter which differs in appearance from the aforesaid types but which functions in similar fashion to them. An example would be in the form of a glass cube which was formed by the cementing together of the hypotenuse faces of two matched glass prisms, each being of the right-angle type with its three optical faces making angles of 45°, 45°, and 90° to each other in respective pairs. The refractive index of the cementing layer is chosen to be less than that of the glass by a certain amount. Rays entering an optical face of the cube and striking the hypotenuse face will then be divided into a transmitted and a reflected component in some ratio which depends upon the relative refractive indices of the glass and cement.

In such a prism, the sum of the reflected and transmitted percentages is essentially unity, with the absorption of light being negligible. In modifications of the prism beamsplitter, the reflectance of the hypotenuse face may be enhanced by use of a thin metallic layer. The absorption of light will then be non-negligible.

In the foregoing discussion, we have emphasized the fact that modern technology allows the preparation of beamsplitters covering a wide range of beamsplitting ratios in terms of the relative partitioning of the reflected and transmitted components. The availability of a choice of beamsplitting ratios is important to our invention in terms of the visual appearance of the final image seen by the observer. For example, if first beamsplitter 12 of FIG. 1 were to be of the "50-50" type in which the reflected and transmitted components were equally intense and with no absorption loss, then the intensities of the rays approaching second beamsplitter 16 would be equal, except for minor optical losses in the intermediate components. If beamsplitter 16 were to be similar to beamsplitter 12 in function, then fifty percent of the beam intensity in the primary ray family and fifty percent of that in the secondary ray family would enter the eye of the observer, the remaining intensity having been diverted elsewhere by beamsplitter 16. The primary and secondary images entering the eye 18 of the observer would then appear equally bright. This would appear to represent an optimal condition for comparing the ellipticities of two orthogonal ellipses.

However, another consideration dictates that it is preferable for the primary image to appear brighter than the secondary image. This is for the reason that the primary image carries with it pictorial information about the corneal region in which the surgeon is simultaneously performing surgical manipulations while comparing the ellipses. The secondary image carries with it the same pictorial information but disposed at right angles to that in the primary image. In order to avoid pictorial confusion, it is desirable that the secondary image be visually suppressed to some extent. Therefore, we suggest that various means may be employed in our invention in order to achieve a secondary image which is less bright than the primary image.

An obvious solution would be the placement of a spectrally neutral absorbing filter anywhere in the secondary path. Its degree of absorption determines the extent to which the secondary image is suppressed with respect to the primary image. Neutral absorbing filters are commercially available in a variety of absorptivity values and may be further combined to achieve values which are intermediate to those which are available. One supplier of such filters is Eastman Kodak Company who provides them under the name "Kodak Wratten Neutral Density Filters".

Another means of controlling the light-intensity ratio between the primary and secondary images is by use of beamsplitters with unequal reflectance-to-transmittance ratios. Here, use is made of the available technology in controlling such ratios. It is merely necessary to ensure that either or both beamsplitters 12 and 16 be provided with a smaller reflectivity value than its transmissivity value. The choice of reflectance-to-transmittance ratio is not critical and is a matter of personal preference by the using surgeon. An example of reasonable values would be 30 percent reflectance and 70 percent transmittance in both beamsplitters. The brightness of the secondary image, with respect to that of the luminous target 11, would be given essentially by the product of the reflectances of both beamsplitters. In this case, the secondary image would contain approximately 9 percent of the intensity in luminous target 11. By the same reasoning, the relative brightness of the primary image would be established by the product of the transmittances of beamsplitters 12 and 16 and would be approximately 49 percent of the brightness of target 11.

The approximately five-to-one image brightness ratio would be interpreted as a lower ratio by the eye, whose sensitivity to brightness variations is not linear. Thus, an image containing one-fifth the radiant power of another image would appear, to the eye, to be nearly half as bright as the other image.

It is equally possible to achieve a desired image-brightness ratio by use of beamsplitters which differ in the amounts of their reflectance-to-transmittance ratios. For example, a "50-50" beamsplitter in combination with a "17-83" beamsplitter would produce essentially the same five-to-one ratio. However, from the standpoint of assembly-line manufacture of our invention, it is preferable to use identical beamsplitters for both functions. This minimizes the required parts inventory and the risk of assembly errors.

Compared with the use of beamsplitters with equal reflectance-to-transmittance ratios in combination with neutral density filters, the afore-described method may be less economical in terms of parts costs. However, it offers advantages in terms of optical efficiency where image brightness is at a premium, because it is less wasteful of light than using absorption filters. The reader will recall that the reason for preferring final images of unequal brightness is to allow the surgeon to distinguish readily between the primary and secondary images and, particularly, to be able to ignore the secondary image visually when he is concentrating on the suturing procedure as seen in the primary image.

A second means of allowing the images to be distinguished is taught by our invention, and that is the means whereby color-coding of the separate images is employed. As an example, a final effect may be achieved in which the primary and secondary images may be rendered distinguishable by being presented in separate colors, such as red and blue, or yellow and white. The color coding method can be applied in situations where both color components are contained in the spectral content of the original light source. If the light source is essentially white, then a large choice of color pairs is available for the primary and secondary images. If the source is highly colored, as would be the case with a neon-lamp or laser light source, for example, the color choice is more restricted. For monochromatic lasers such as a helium-neon laser emitting only red light, color coding cannot be employed.

An obvious means of achieving color coding in the primary and secondary images would be by the use of the aforesaid beamsplitters in combination with separately colored transmission filters inserted in the respective primary and secondary ray paths. Most conveniently, color filtering would be provided by use of colored glass filters such as are provided by Corning Glass Works and others, or by use of colored gelatin sheet filters provided as Wratten filters by Eastman Kodak Company. Nonabsorbing optical interference filters, known in the optical art, may also be used but are more costly.

Alternatively, a more costly but also more optically efficient choice would be the use of "dichroic" beamsplitters in preferance to ordinary beamsplitters used alone or in combination with colored filters.

A dichroic beamsplitter is a beamsplitter which effectively transmits one group of colors with high optical efficiency while reflecting its complementary color group with equally high efficiency. An example would be a beamsplitter which was prepared so as to transmit essentially red light while reflecting essentially blue light. Such beamsplitters are designed and fabricated by the same methods as are used in preparing dielectric multilayer interference beamsplitters which were referred to earlier in this disclosure. One feature of their design is that, being angle sensitive, the user must specify not only the color properties which he desires but also the angle at which the beamsplitter is to be used with respect to the incident light beam. By proper design of a dichroic beamsplitter, the fabricator not only can achieve the desired colors but can control their relative brightnesses as well. Dichroic beamsplitters may be obtained as stock items or as custom-fabricated items from various manufacturers who are listed in optical industry directories available at technical libraries.

Continuing our discussion, we refer now to element 14 of FIG. 1, shown as a dove prism which is intended to illustrate one form of image rotator whereby an image-bearing family of light rays may be rotated about its axis through an arbitrary angle from zero to 360°.

The operation of an image rotator is explained as follows. If one were to place an ordinary mirror face up on a table before him or her and were to examine the image of an object on a far wall, he or she would observe this image to be inverted with respect to the actual object. If the observer were to raise this mirror to eye-level while, at the same time, rotating it in a circular arc to a vertical position, while observing the image of the same object as seen at a glancing or grazing angle, the image would appear to right itself but to become reversed from right to left. By continuing this process until the mirror was above eye-level and face-down, one would observe the image of the same object to again appear inverted. The process would then be repeated as the mirror continued to be swung in an arc in the same direction until it reached the original tabletop, face-up position.

In performing this experiment, one will observe a certain difficulty in manipulating the mirror so that the image of the desired object is always within view. The mirror must be observed at a fixed, oblique angle while being moved through a prescribed arc and being rotated about its own plane at the same time.

In the historical development of the present optical art, various devices have been introduced which can provide image rotation more conveniently than by use of the aforesaid single mirror. One such device is the dove prism. Another is called variously the "K-mirror" or the three-mirror image rotator. The dove prism is a solid, truncated prismatic optical element, such as of glass, which in cross-section, is dovetailed in shape. The K-mirror is a system of three full-mirrors in such relationship as to resemble an upper-case English letter "K". Both devices offer the convenience of being able to rotate the image of an object while being located directly on the axis between the object and the eye. In this way, the device need undergo only a rotation, without having to be simultaneously and carefully manipulated through an arc. In both devices, the effect of two angular deflections and one right-to-left reversing reflection is achieved. The deflections are achieved via the prismatic faces in the dove prism and via the K-arm mirrors of the K-mirror. The reversing reflections are achieved via an internal reflection by the long face of the dove prism and by a mirror reflection in the central mirror of the K-mirror. The long face of the dove prism is referred to as the hypotenuse face because it is the hypotenuse of the basic triangle of which the dove-prism cross-section is a reduced or truncated part. Both devices are in common use in modern optical practice.

A recent technical discussion of the K-mirror, with references to the dove prism, appears in the journal *Applied Optics*, Volume 18, No. 23, pages 3883-3884, Dec. 1, 1979.

Figure 3:
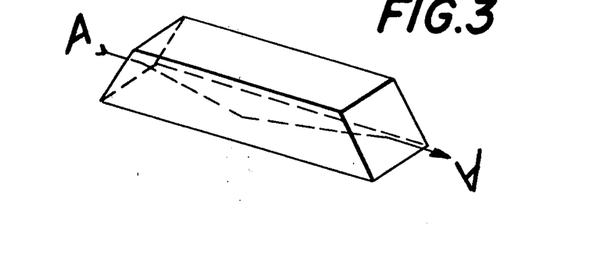
FIG. 3 is a drawing showing the optical behavior of a dove prism, which prism typifies one form of optical image rotator which is an essential ingredient in our invention.

The image-inverting capability of the dove prism is illustrated in FIG. 3, which is self-explanatory.

Essentially, the functions of the dove prism and of the K-mirror are identical. In practice, there are minor differences in their features which must be taken into account in any selection between them for optical design purposes.

It is a feature of the dove prism that it suffers from chromatic aberration. This is produced as a result of the fact that light rays, upon entering the first surface and upon leaving the second surface, are refracted through differing angles, depending upon their wavelengths or colors. The result is that the red components of a light-ray family do not follow exactly the same optical path through the dove prism as do the blue components of the same light-ray family. A consequence of this result is that any final image which is formed of such a light-ray family may exhibit color aberrations in which objectionable red and blue colored fringes may appear within image parts which should ordinarily be white. There are situations, however, in which this objection is either tolerable or is not noticeable due to the nature of the final image. It is a feature of the K-mirror that perfectly achromatic transmission is effected, due to the property of the reflecting elements that all wavelengths are deviated through identical angles.

Another difference between the dove prism and the K-mirror concerns the optical path length. The path length traversed by a light ray in an optical system is often an important consideration in the design of the system. In a focusing system containing lenses, such as in a microscope ocular, the placement of lenses so as to obtain properly focused images depends critically upon the optical path lengths which are traversed by the image-forming rays before they reach one or more of the lenses. In the K-mirror, the total optical path length traversed by the light rays is simply the arithmetic sum of the distances between the three elements of the mirror at the points where each ray is reflected. This is referred to as the geometrical path length. In the dove prism, the optical path length is the geometrical path length multiplied by the refractive index of the prism material. For a dove prism fashioned from optical glass with a refractive index which is typically 1.52, the optical path length is 1.52 times the geometrical path length. If the refractive index of the material differs by an uncertain amount from 1.52, then the optical path length will have an uncertain value by the same amount, with this uncertainty being a burden to the optical system designer. A further complication is brought about by the fact that the optical path lengths will differ for differently colored components in the traversing light beam. This is because such components traverse different geometrical paths through the prism and, moreover, these path lengths must be multiplied by different values of the refractive index in order to yield the optical path length values. It is a physical property of most optical materials that their refractive indices are wavelength-dependent.

A third difference between the dove prism and the K-mirror is that the two refracting faces of the dove prism inevitably exact a toll in reflected light loss by virtue of their surface gloss or sheen. The amount of this loss is in proportion to the refractive index of the optical material, be it glass or otherwise. Its exact amount is calculable by well-known optical formulae. In certain instances, such reflective loss need be of no concern. In cases where it is of concern, it may be suppressed by the use of antireflection coatings which are known in the optical art, but which are costly and inconvenient to provide. It is thus an advantage of the K-mirror that no such reflectance problem is offered.

For mass production purposes, it is an advantage of the dove prism that it may be fabricated in one solid piece, via conventional molding and optical finishing processes, so as to produce identical pieces by machine with little human intervention. It is correspondingly a disadvantage of K-mirror fabrication procedures that the individual elements must be separately aligned and tested for alignment. However, it is possible that in some future time, K-mirror fabrication may be achieved with perfect alignment, not requiring human intervention, by plastic-molding replication processes which are currently under development in the optical industry.

One disadvantage which must be pointed out in the use of K-mirrors is that the reflecting surfaces exhibit a certain susceptibility to damage by abrasion and to contaminating deposits. This is because they are inevitably fashioned from first-surface mirrors in order to avoid undesirable ghost images. The reflecting surfaces, being delicate, must be cleaned with great care as ordinary contamination periodically accumulates on them. Moreover, unless the reflecting surfaces are prepared to exacting standards, some light loss will occur upon each reflection, the result of which will be cumulative after the three usual reflections have occurred in the K-mirror. If substantial light loss cannot be tolerated in a particular use of the invention, the dove prism may be an advantage because its single reflection at the hypotenuse face is carried out at exactly 100% efficiency. This efficiency in the dove prism will be diminished only to the extent that the entrance and exit faces may exhibit a given reflectance loss.

It is a property of both the dove prism and the K-mirror that either may be used at such axial orientation angles as to provide an erect image, as opposed to an inverted one, and to serve primarily as a path lengthener instead of an image rotator. Either device may thus serve the purpose of the path lengthener 17 which is shown in FIG. 1 as a K-mirror. It is necessary to ensure, however, that the device is properly configured so as to provide exactly the needed amount of optical path length increase in the primary light ray path to equalize the length with the secondary path. Proper equalization is achieved when the primary and secondary images as seen by the observer are in the same plane and free from parallax.

In embodiments of our invention, it is advantageous to use a K-mirror as a path lengthener. The independence of its various members allows for convenient adjustment of the path length by simple repositioning of one or more members. The K-mirror may thus be used to optimize the path length increase, and the K-mirror parameters may then be used in the design of a dove prism or other prismatic element of fixed dimensions. It is known in the optical art that solid optical elements having shapes other than that of the dove prism may also be used as beam path lengtheners.

The following are further features of the dove prism and the K-mirror which are of interest whether these devices are used as image rotators or as path lengtheners.

A disadvantage of the dove prism is that its angular field of view is relatively restricted by comparison with a K-mirror. When necessary, it is a common practice to double the available aperture due to a single dove prism by cementing together two identical such prisms at their hypotenuse faces. It is necessary, however, to optically isolate the individual prisms by providing a highly reflecting coating between them at the hypotenuse faces. This is conveniently done by the application of a vacuum deposited metallic layer on one of the hypotenuse faces prior to their being joined.

The entrance and exit faces of a dove prism must remain substantially clean for best optical performance, as with the elements of the K-mirror and with other optical elements in the system. When a dove prism is used individually, as opposed to being combined with a second dove prism, its hypotenuse face must be maintained scrupulously clean. Moreover, this face must not be in optical contact with other surfaces lest the total internal reflective action, which is responsible for the behavior of the dove prism, be interfered with. This requirement places a burden on the mechanical design of a mounting arrangement for the prism. Such a mount must be designed so as not to contact the active area of the hypotenuse face.

We refer now to the image-rotating function which is performed by element 14 of FIG. 1, shown there as a dove prism. We remind the reader that the angular orientation of the secondary image, as viewed by the observer, is fully dependent upon the angular orientation of the image-rotator about its own optical axis. For purposes of clarity in FIG. 1, we have shown the dove prism in cross-section and the refracted ray paths at the entrance and exit faces. At the same time, we have shown the total internal reflection which occurs at the hypotenuse face. With the dove prism as shown in FIG. 1, the final secondary image will exhibit a left-to-right reversal instead of the 90° rotation which is used in the preferred embodiment of our invention. In order to achieve the recommended rotation, one must orient the dove prism at an axially rotational angle which is displaced by 45° from the orientation shown in FIG. 1. The angular displacement may be in either of the clockwise or counterclockwise senses, depending upon whether the final secondary image is to be rotated clockwise or counterclockwise relative to the primary image. In our preferred use of the invention in which ellipticity comparisons of circle-like figures are to be made, the effectiveness of the comparison is fully indifferent to the sense of the rotation.

Figure 4:
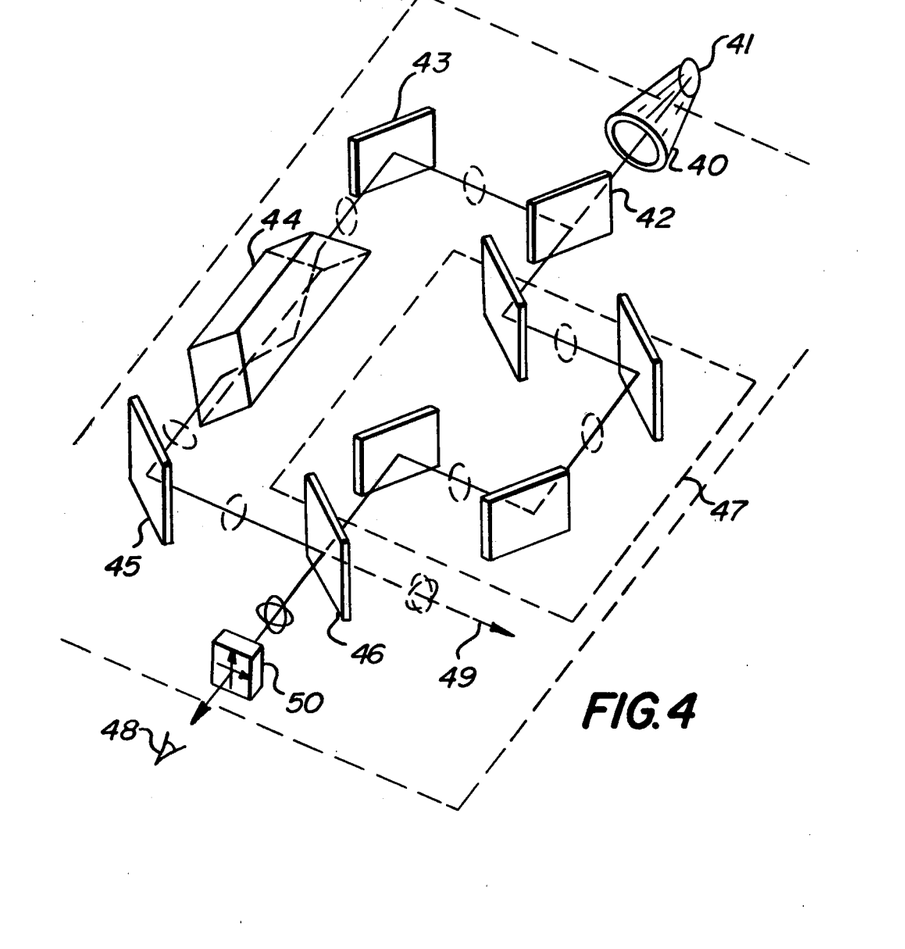
FIG. 4 is a perspective view of the preferred embodiment of the invention.

The preferred orientation of the dove prism is shown in FIG. 4, which is a perspective view of our preferred embodiment to be described hereinafter.

The indicated precaution about angular orientation applies equally well to the path lengthener which is shown as K-mirror 17 in FIG. 1. As shown, the K-mirror is properly oriented to serve the purpose of our invention. By this, we mean that the geometrical plane which contains the reflected segments of the system optical axis coincides with the plane containing the reflected axial components of the secondary rays. Thus, path lengthening occurs without image rotation, as is intended. Optionally, the K-mirror can be angularly displaced through 180° about its axis with no effect on the resulting primary image. The K-mirror axis is taken here to contain the axes along which the incident and emergent rays propagate.

Where it may suit the purpose of the application, an embodiment of the invention may be constructed in such manner that the K-mirror is oriented arbitrarily about its axis so as to provide a desired amount of image rotation in addition to the desired path length increase. The dove prism may likewise be arbitrarily oriented about its axis. As an example, we consider the case where the K-mirror is displaced angularly, about its axis, by an angular value of $22\frac{1}{2}°$ from the position indicated in FIG. 1, such displacement being carried out in the clockwise sense. If, again for example, the dove prism were to be angularly repositioned from the orientation shown through an angle of $22\frac{1}{2}°$ in the counterclockwise sense, then the resulting primary and secondary images will each have been displaced through 45° in opposite senses and will be perceived as being disposed at right angles to each other although no longer parallel to the horizontal and vertical planes.

As incidental feature of our invention is that, in certain embodiments, it may present to the observer images which are reversed in the left/right sense with respect to the target. This effect comes about through the optical phenomenon of mirror reflection wherein a singly reflected image will suffer such a reversal. It is moreover true that an image which has been reflected sequentially by an odd number of mirrors will suffer the same reversal. Contrariwise, multiple sequential reflection by an even number of mirrors yields an image of the proper right/left orientation. The dove prism which exhibits a single reflection and the K-mirror which yields three reflections will both cause image reversal in addition to any rotational displacement.

In the embodiment shown in FIG. 1, it will be seen that the primary ray path, as intercepted at the eye 18 of the observer, will have traversed two beamsplitters as well as the triply reflecting K-mirror. The net number of reflections in the total path is thus the odd number "three", yielding a reversed primary image at the eye 18.

In the secondary ray path, a total of five reflections is achieved by the combination of the beamsplitters 12 and 16, the full mirrors 13 and 15, and the dove prism 14. Again, the secondary image will be reversed with respect to the target 11.

It is conceivable that such image reversal may be undesirable in certain uses of the invention. In such cases, it will be apparent to optical designers that the judicious application of one additional reflecting surface in the common primary and secondary path portions will correct the undesired reversal. The additional reflection may be achieved by another mirror or by any of several prism types which are known to optical practitioners.

In certain instances, the image reversal may be objectionable only in the case of the primary image whereas such reversal may be a matter of indifference with regard to the secondary image. We therefore teach a method of correcting primary image reversal by a convenient means. Said means is to replace the three element K-mirror system of FIG. 1 with a four mirror path lengthener. It will be obvious to optical design engineers how to dispose said four mirrors at the corners of a rectangle so as to replace the triangular path deflection as shown in FIG. 1 by a rectangular path deflection. Said means of such mirror disposition will become clearer in our subsequent description of FIG. 4.

Alternatively, we call attention to the ray family 19 in FIG. 1, herein designated as residual rays, which were referred to earlier in this disclosure as serving no immediate purpose to the invention. We have pointed out that these rays are nonetheless available for further use by one or more additional observers, such as via a second microscope ocular, a television camera or the like.

At the beamsplitter 16, the primary and secondary rays, which are to comprise the residual rays 19, will suffer, respectively, one more and one less reflection than their counterparts which proceed to the eye 18 of the principal observer. It will thus be understood that the final primary and secondary images which result from residual rays 19 will indeed have suffered no net image reversal. Optionally, the principal observer may choose to view the final images along the ray path 19 instead of from position 18 as shown in FIG. 1.

If, in a particular embodiment, it occurs that second beamsplitter 16 is prepared as a dichroic beamsplitter, then the final images as viewed from the two aforesaid positions will be differently colored. If the beamsplitter is of the colorimetrically neutral type, no such color difference will occur.

We refer, now, to a previous part of this disclosure in which was treated the desirability of either color-coding or reducing the brightness of the secondary image so as not to interfere with surgical manipulations performed with the aid of the primary image.

A further teaching of this invention is the possibility of providing an image-occluding feature which may, at the will of the operator, be made to obscure the secondary image completely. The activation of this feature, depending upon which embodiment is selected, may be achieved either by manual operation of a lever, knob, pushbutton, foot pedal control or an automatic timing mechanism which periodically occludes the secondary image for a predetermined time period, or by various other means and contrivances which will be apparent to a mechanical system designer. The intended control device for the occluding provision, be it a lever or foot pedal or other means, may be designed to be connected mechanically to the occluding member or to operate via an electrical circuit which brings about a mechanical motion by use of a solenoid or other transducer of electrical power to mechanical motion.

The occluding action may itself be brought about in a variety of fashions. A method which is preferred for its simplicity is to activate an opaque flag or shutter. It can be introduced at any convenient point in the secondary ray path to obscure the path fully. The secondary path is defined as originating at the reflecting surface of first beamsplitter 12 of FIG. 1 and terminating at the reflecting surface of second beamsplitter 16.

Said occlusion may also be achieved by rotation of any of beamsplitters 12 and 16 or of mirrors 13 and 15 in such manner as to deflect the secondary ray path out of its normal course and into some direction where the light rays may be absorbed by a prepositioned optical absorbing medium having, for example, a black, velvet-like surface.

It will be recognized by optical system designers that another means may be provided so as to allow the observer to distinguish between the primary image alone and the perceived combination of the primary and secondary images. This means would provide the desirable advantage of not requiring a mechanical or electromechanical action in order to achieve the occlusion. Instead, an optical "split field" provision would allow the operator, via a slight sideways displacement of his or her eye, to distinguish between the primary image and the combined primary and secondary images.

The split field provision may be accomplished by any of a variety of methods which are practiced in the design of optical systems. These will not be elaborated upon here but will be illustrated by a basic example. Referring again to FIG. 1 and, in particular, to second beamsplitter 16, we consider the situation in which one-half or the other of said beamsplitter, as shown, is removed. If the eye 18 of the observer is repositioned laterally so as to receive those light rays which have bypassed the remaining portion of beamsplitter 16, the observer will witness only the primary image. A lateral displacement of the eye 18 in the opposite direction will enable the observer to perceive the combined primary and secondary images.

Alternatively, the original second beamsplitter 16 may be provided with a central opening through which pass only the primary rays, with the remainder of the beamsplitter area providing the combining function. In this example, the primary image alone will be observed when the eye 18 is positioned on or near the system optical axis. At other positions, the eye will perceive the combined images.

Thus far in our discussion, we have indicated an advantage of our invention to be a convenient means of allowing the user to assess visually the degree of ellipticity in a near-circular figure. We have not implied the use of any means whereby the degree of ellipticity may be quantified by use of measurement means. However, it is understood that various measurement scales, provided in the form of eyepiece reticles, are often used in microscopes for measurement purposes. It is therefore suggested that such scale reticles are easily adapted to our invention so that the observer may have reference to standard measurement units in assessing the degree to which a supposedly circular figure departs from circularity. In mathematical parlance, the degree of such a departure is termed "eccentricity" when such departure results in an elliptical configuration. Eccentricity is a quantity related to the ratio of lengths of the longest and shortest axes of an ellipse. It derives its name from the fact that various arc segments of an ellipse may be likened to portions of circles whose centers are not concentric, as opposed to the case of a true circle, all of whose arc segments are centered at a given point. The proposed measurement scale may thus be configured in units of eccentricity, so as to allow the observer to quantify the degree by which an elliptical figure departs from circularity.

The scale may be quantified in units other than eccentricity such as in standard English or in metric length units or others. A convenient choice of units for the ophthalmic surgeon would be dioptric units. A diopter is a measurement unit which is used in optometric practice and by means of which the refractive, or light bending, powers of various spherical optical surfaces may be compared. It is a feature of optical elliptical surfaces that their dioptric powers will differ in the orthogonal planes containing the major and minor axes. The degree of difference determines the amount of astigmatism occurring in an image which has been focused by such a surface. As such, it is convenient for the opthalmic surgeon to assess the degree of ellipticity of an ellipse in units of diopters, a quantity to which he is accustomed in his daily practice. Therefore, in the preferred embodiment a measurement scale could be provided as an eyepiece reticle with a scale calibrated in dioptric units so as to provide the ophthalmic surgeon with a convenient form of information with which he may correct, by proper suturing, the observed degree of astigmatism in the cornea of a patient.

An important consideration in the disclosure of this invention concerns the concept of "axis of rotation" of a geometrical figure and the matter of where such an axis is to be located. If one is to assess the degree of ellipticity in a near-circular figure by the means taught in our invention, one recognizes intuitively that the doubled images should be presented with a 90° relative rotation about their common center. By this means, the major and minor axes of the secondary image are caused to fall upon the minor and major axes of the primary image, respectively, thereby allowing ready comparison of the lengths of the axes of the ellipses. Were the secondary image to be rotated about some axis other than its central one, the rotated secondary image would be displaced laterally from its primary image counterpart and the aforesaid comparison could not be as readily performed.

Concentricity of the relatively rotated primary and secondary images is ensured when two conditions are met. These conditions are as follows:

1. The microscope is so positioned over the eye of the patient that the reflected image of the luminous target is centered on the microscope optical axis; and
2. The image rotator has been rotated about the proper axis.

The proper axis is the axis which coincides with the extension of the microscope optical axis as reflected in first beamsplitter 12 and again in first full mirror 13 and, therefore, entering the image rotator 14 as shown in FIG. 1.

According to the teachings of the invention, it is therefore necessary not only to construct the embodiment in a proper manner but it is likewise necessary to ensure the proper use of the embodiment in order to derive maximum benefit therefrom. In particular, the user must ensure that the luminous target which is reflected in the patient's eye is perfectly centered within the field of view or, more correctly, on the central axis of the microscope system. Such centering is most readily carried out by the proper positioning of the microscope over the eye of the patient. Any departure from correct centering will be perceived as a departure from concentricity of the doubled images, and this perception will aid the user in adjusting the microscope position correctly. As a convenience in performing this adjustment, we indicate here that foot pedal operated electromechanical positioning controls are readily adaptable to this purpose, being widely known in the mechanical positioning art.

FIG. 4 is a perspective drawing of the preferred embodiment of our invention. The drawing is intended to make clear various features which are illustrated in the schematic diagram shown in FIG. 1. However, certain elements of the FIG. 1 portrayal have been intentionally altered in FIG. 4 for reasons which will be made clear presently.

In FIG. 4, the various numbered items are in a corresponding relationship to the numbered items in FIG. 1, with the second digit in the two-digit designations being in agreement in both figures.

The first notable difference between FIG. 1 and FIG. 4 is observed in the disposition of the image rotator shown, respectively, as items 14 and 44 in the separate drawings. In the first such drawing, in which it is intended to portray the optical configuration of light rays traversing a dove prism, the prism is shown in such rotational orientation as not to effect an image rotation but merely a right-to-left reversal with respect to target 11. In FIG. 4, the image rotator 44 is disposed at a preferred angular orientation about its axis so as to provide a 90° rotation of the image bearing rays passing through it. In said preferred angular orientation, the geometrical plane which contains the hypotenuse face, or totally internally reflecting face of the prism, is oriented 45° away from the geometrical plane which contains the primary and secondary axes of the optical system.

The second notable difference between FIG. 1 and FIG. 4 concerns the configuration of the path lengtheners 17 and 47, respectively. For expository purposes, we have shown path lengthener 17 as a three mirror system which provides for convenient adjustment of the desired path length increase but which also imposes a net image reversal upon the finally observed image with respect to target 11. In FIG. 4, we portray path lengthener 47 as a four mirror system which, by comparison with element 17, will produce no net reversal of the primary image with respect to target 41.

Also shown in FIG. 4, for purposes of exposition, is an unnumbered superposition of ellipses shown in dashed-line representation. In this superposition, we intend to convey the sequence of angular orientations which is undergone by the undeveloped or "not yet focused" light ray families which proceed from target 41 until they are intercepted by the eye 48 of the observer and are perceived as fully focused and comprehensible images. It will be observed that the ellipses associated with the primary ray path remain unchanged in angular orientation relative to target ellipse 41 whereas those which have passed through image rotator 44 have suffered a 90° rotation. The separate ellipses are then combined at beamsplitter 46 and proceed through other refractive elements whereupon they ultimately reach the eye of the observer as a superposed pair of perpendicularly disposed images.

The preferred embodiment of the present invention functions in the following manner. Referring to FIG. 4, a light source 40, constructed so as to permit the image forming rays reflected from the target 41 to pass through a central opening uninterrupted and unimpeded, is disposed circumferentially about the microscope objective lens. The light source 40 is designed so as to illuminate the target 41 with a ring of light. The light source 40 can be constructed in any manner known in the art to provide the circular illumination of the target 41. The light reflected from the cornea or target 41 passes through the microscope objective lens 40 to a first beamsplitter 42. The beamsplitter 42 is disposed at an angle of 45° to the optical path of the image forming rays reflected from the target 41. The beamsplitter reflects a predetermined portion of the image forming rays through an angle of 90° creating a secondary ray family. The remainder of the image forming rays is permitted to pass through the beamsplitter 42 creating a primary ray family.

The secondary ray family undergoes a 90° deflection by full mirror 43, an image rotation of 90° by dove prism 44, and another 90° deflection by full mirror 45 before being recombined with the primary ray family at beamsplitter 46.

The primary ray family undergoes a geometric path lengthening by path lengthener 47 to allow the resulting images of both primary and secondary ray families to appear in the same plane and be in focus to the eye 48 of the observer.

The primary ray family and the secondary ray family are recombined by beamsplitter 46 providing images which will pass through reticle 50 to the eye 48 of the observer and image 49 which can be used in a manner similar to that described above for image 19. The reticle 50 has a scale for measuring the eccentricity of the circularity of the combined primary and rotated secondary images. The scale can be divided into units based on any known measurement scheme, however, dioptric units are preferred. In order to properly be able to measure the eccentricity of the cornea it is preferred that the primary image and the secondary image be visually distinguishable. This can be accomplished by modifying the preferred embodiment by adding further elements or changing already described elements, either individually or in combination with one or more modifications.

Figure 4A:
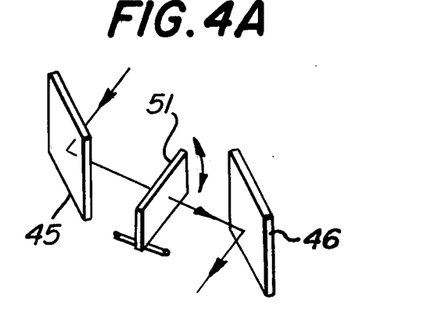
FIG. 4A is a perspective view of a modification of the preferred embodiment of the invention showing an opaque shutter interposed in an optical path.

Referring to FIG. 4A, the secondary ray family can be entirely blocked by an opaque shutter to provide distinction between the images. The shutter 51 can be either a guillotine type which slides into the optical path, or a rotary type, which pivots into the optical path. The mechanism for triggering the shutter 51 may be any known in the mechanical arts as described above. It is preferred that no part of the shutter 51 or its control mechanism impede the transmission of any of the light rays while the shutter is not blocking the optical path.

Figure 4B:
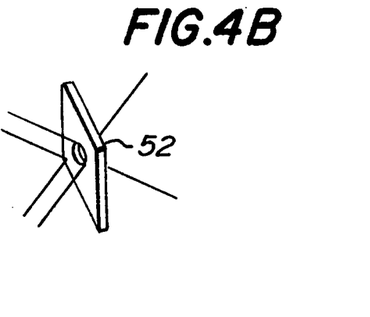
FIG. 4B is a perspective view of a modification of the preferred embodiment of the invention showing a central opening in the second beamsplitter creating a visual split field.
Figure 4C:
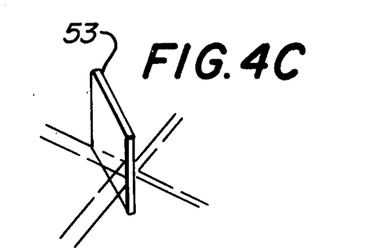
FIG. 4C is a perspective view of a modification of the preferred embodiment of the invention showing the halving of the second beamsplitter creating a visual split field.

Another method of distinguishing the images is to create an optical split field. This can be done by modifying the second beamsplitter 46 to include a central opening 52 therein. The central opening 52 will allow the light rays of both the primary and secondary ray families to pass through without deflection and, thus, without recombination. The area surrounding the central opening 52 will provide for the deflection and transmission, described above. The observer can position his eye so that he can either view both images superposed upon one another or the primary image separately. See FIG. 4B. Another modification to achieve a visual split field is to halve the second beamsplitter 46. In decreasing the size of beamsplitter 46 the half that remains also retains its former position. Thus, a portion of each ray family will no longer be deflected. The observer, as described above, can, by moving his eye, observe both images superposed on one another or the primary image alone. See FIG. 4C.

Figure 4D:
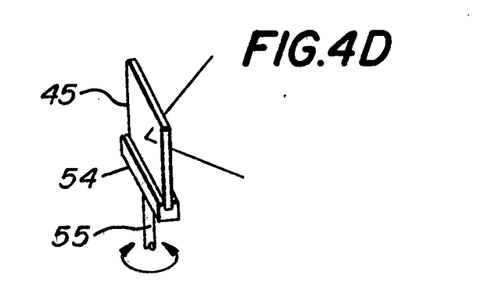
FIG. 4D is a perspective view of a modification of the preferred embodiment of the invention showing the rotation of an element in an optical path to deflect the light rays out of such path.

Referring to FIG. 4D, any of the mirrors or beamsplitters in the secondary optical path can be rotated to deflect the secondary light rays away from the prescribed path. Depending on the amount of rotation and which element is rotated the visual intensity of the secondary image will be superposed or become nonexistent. It is preferred to rotate one of the full mirrors 43, 45. The full mirror is mounted on a bracket 54 having a connecting rod 55 to a control mechanism for rotating the mirror. The control mechanism can be any of those known in the mechanical art as described above. While the mirrors can be rotated in either direction, it is preferred that the rotation of the mirror deflect the rays toward the light absorbing walls of the housing to prevent interference with the primary image.

Figure 4E:
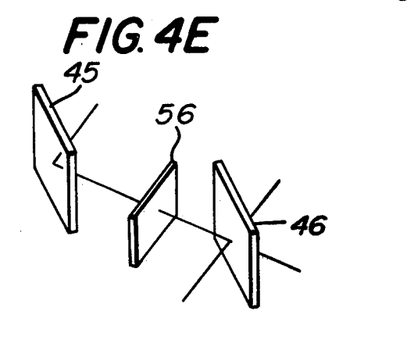
FIG. 4E is a perspective view of a modification of the preferred embodiment of the invention showing a spectrally neutral absorbing filter interposed in an optical path.

The primary and secondary images can also be distinguished by decreasing the intensity of one or the other. Referring to FIG. 4E, a spectrally neutral absorbing filter 56 is interposed in the secondary optical path between mirror 45 and beamsplitter 46. The filter 56 will absorb a certain portion of the light rays of the secondary ray family without affecting any of its color characteristics. Thus, a visually suppressed secondary image results form the deflection of the secondary ray family by beamsplitter 46. It is preferred that the filter 56 be placed in the secondary optical path to visually suppress the secondary image. Of course the secondary image may also be reduced in intensity by substituting beamsplitters having unequal reflectance-to-transmittance ratios. It is preferred that the reflectance be less than the transmittance in order to suppress the visual intensity of the secondary image. Either or both beamsplitters 42, 46 can be so modified in accordance with the above description.

Figure 4F:
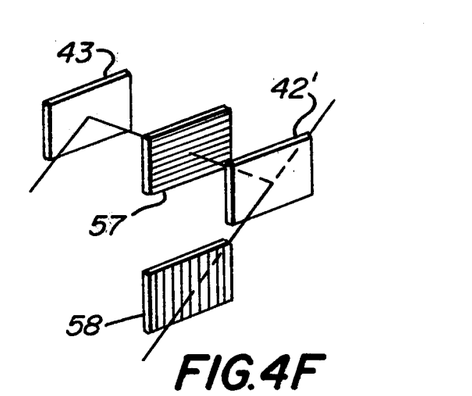
FIG. 4F is a perspective view of a modification of the preferred embodiment of the invention showing the substitution of a dichroic beamsplitter and the interposing of differently colored light transmissive filters into the optical paths.

The final method of distinguishing the primary and secondary images which will be discussed in accordance with this invention will be the color coding of each of the images. Referring to FIG. 4F, color coded light transmissive filters 57, 58 can be interposed into the secondary and primary optical paths, respectively.

If the light source 40 is a white light source the choice of colors to be used in coding the primary and secondary images is freer than if the source 40 is colored. We prefer in the instance where color coding is to be used to distinguish the primary and secondary images that a light source 40 provide white light. In accordance with the above discussion concerning color coding of the images, filter 57 would be interposed between first beamsplitter 42 and full mirror 43. Filter 58 would be interposed between beamsplitter 42 and path lengthener 47. While we prefer that the filters 57, 58 be placed in the positions described, they can be placed in any location in either optical path before the rays are recombined. The choice of colors for the filters is determinant upon the color of the light source and the visual distinguishability of the colors. An alternate choice would be the use of dichroic beamsplitters. Beamsplitter 42', a dichroic beamsplitter, may be substituted for beamsplitter 42. The dichroic beamsplitter 42' is able to transmit one color light while reflecting its complementary color group. In FIG. 4F a dichroic beamsplitter 42' is used for transmitting essentially red light while reflecting essentially blue light. In order that only these colors are transmitted over the respective optical paths filters 57, 58 of like colors are interposed in the respective optical paths. It should be noted that either of the elements alone or both elements in combination will result in color coding of the images giving the observer the capability to distinguish the primary from the secondary image based on color.

It is understood from the above discussion that the elliptical images of the superposed pair may be separately colorcoded or brightness coded for easy identification by the insertion of suitable colormodifying or brightness-modifying means in one or the other of the primary and secondary paths.

It will be evident to optical system designers that the exact physical dimensions and placements of the various optical components which are depicted in FIGS. 1 and 4 will be predetermined by the optical geometry of the particular microscope with which our invention is to be used. Preferably, the optical elements of our invention will be configured as an integral part of the microscope ocular. In most microscopes, the ocular is a withdrawable member which serves to further magnify the aerial image which is formed by the microscope objective lens. As such, the ocular is provided as an interchangeable member which is readily replaceable by a similarly configured ocular but having a different magnifying capability. In ordinary microscopy practice, it is customary for the practitioner to select a different ocular magnification, when desired, by the replacement of one ocular with another.

A typical microscope ocular consists of one or more lenses in a specific geometrical arrangement in which lenses are mounted within an essentially tubular supporting structure. This structure is typically one inch or so in diameter and a few inches in length. The structure outer diameter is matched to the inner diameter of the microscope tube so that the ocular structure will slide readily into the tube and will thus be secured by a combination of gravitational and moderate frictional influences. External stops on the ocular outer wall ensure that the ocular will be inserted into the microscope tube by the proper distance as determined by focusing requirements. The remainder of the ocular remains projecting above the upper rim of the microscope tube, its diameter often exceeding that of the lower portion.

Various design options are available as to the matter of how our invention is to be incorporated into a given microscope ocular. The various optical elements of our invention may be disposed above, below, or between the various optical elements of a given eyepiece, subject to the choice of the optical designer who will be following prescribed design procedures according to the optical geometry features of a given ocular. These features will determine the physical dimensions and placements of the various elements such as the mirrors, beamsplitters and the like.

A consideration which the designer must take into account is that the optical elements of our invention should in no way limit, obstruct or interfere with those light rays which pass normally through the various lenses which comprise the eyepiece. Were such limitation, obstruction or interference to occur, either the angular field of view of the eyepiece could become restricted, thus limiting the observer's eye position to a narrow range, or portions of the image field could become obscured. It will be apparent to optical designers that the optical elements of our invention must be large enough to pass all rays which are intended to be passed by the ocular system, while such elements as the image-rotator and path lengthener must be sufficiently removed from the central axis of the ocular so as not to block any rays at the edges of the ray family passing through the ocular. These elements may be displaced to either side of the central ray family by a sufficient amount, and yet remain within the enclosure of the ocular, provided that the diameter of that part of the ocular which is external to the microscope tube is sufficiently increased. Alternatively, tubular or rectangular lateral extensions may be provided in the ocular sidewalls to allow provision for the placement of components which must be so sideways displaced.

The present invention may be embodied in other specific forms without departing from the spirit or essential attributes thereof and, accordingly, reference should be made to the appended claims, rather than to the foregoing specification, as indicating the scope of the invention.

We claim:

1. An optical device for measuring the sphericity of the corneal tissue in a vertebrate eye whereby an astigmatic condition can be detected and measured comprising a light source for illuminating a target which reflects image-forming rays which travel over a primary optical path, said image-forming rays being divided by a first beamsplitter means creating a primary ray family and a secondary ray family yielding a primary image and a secondary image respectively, said secondary ray family travelling along a secondary optical path and being rotated axially about its axis of propagation through a specifically defined angular displacement relative to the angular displacement of the primary ray family by an image rotating means, and said primary and secondary ray families being combined by a second beamsplitter means creating a combined superposed image formed from said primary image and said secondary image rotated relative to said primary image which may be visually compared and measured in order to determined sphericity of the corneal tissue.

2. An optical device in accordance with claim 1 wherein said image-forming rays reflected from the target form a circular image when reflected from a spherical cornea and exhibit an eccentricity and form an elliptical image when reflected from a non-spherical cornea, said target being the corneal tissue.

3. An optical device in accordance with claim 1 wherein said combined superposed image formed from said primary image and said secondary image rotated relative to said primary image is visually compared by a means for measuring the eccentricity of the circularity of the primary image with the rotated secondary image to determine sphericity of the cornea.

4. An optical device in accordance with claim 3 wherein said measuring of the eccentricity of the circularity of the primary and secondary images is performed by a reticle in an ocular of an optical instrument, said reticle having a scale for measurement of said eccentricity in dioptric units.

5. An optical device in accordance with claim 1 wherein said optical device is housed within a microscope ocular.

6. An optical device for measuring the sphericity of the corneal tissue in a vertebrate eye whereby an astigmatic condition can be detected and measured comprising:

a light source for illuminating a target which reflects image-forming light rays which travel over a primary optical path;

first beamsplitter means for deflecting a predetermined portion of the image-forming light rays emanating from the target through a predetermined angle away from the direction of the primary optical path and permitting the remainder of the image-forming light rays emanating from the target to pass through said first beamsplitter means uninterrupted, said remainder of the image-forming light rays forming a primary ray family and said predetermined portion of the image-forming light rays forming a secondary ray family;

first mirror means for deflecting the secondary ray family through a predetermined angle so that the primary ray family and the twice deflected secondary ray family are parallel and travelling in the same direction over separate optical paths;

image rotating means for rotating the secondary ray family through an angle of 90° about its propagation axis;

second mirror means for deflecting the secondary ray family through a predetermined angle toward the primary optical path;

path lengthener means for lengthening the primary optical path so that the total length of the optical paths travelled by the primary ray family and the secondary ray family are equal so as to provide a primary image and a secondary image in the same viewable plane, said primary image is the resulting image of the primary ray family and said secondary image is the resulting image of the secondary ray family;

second beamsplitter means for deflecting a predetermined portion of the secondary ray family through a predetermined angle into the direction of the primary optical path, permitting the remainder of the secondary ray family to pass through said second beamsplitter means uninterrupted, deflecting a predetermined portion of the primary ray family through a predetermined angle away from the direction of the primary optical path into the same direction as the remainder of the secondary ray family, permitting the remainder of the primary ray family to pass through said second beamsplitter means uninterrupted, thus combining the secondary ray family with the primary ray family so that they result in a superposed image of coincident image-forming light rays formed from said primary image and said secondary image rotated 90° with respect to said primary image;

whereby the recombined superposed image formed from said primary and said rotated secondary images are transmitted and magnified as they pass through an optical instrument having a means for visually comparing and measuring the superposed image in order to determine sphericity of the corneal tissue.

7. An optical device in accordance with claim 6 wherein said image-forming rays reflected from the target form a circular image when reflected from a spherical cornea and exhibit an eccentricity and form an elliptical image when reflected from a non-spherical cornea, said target being the corneal tissue.

8. An optical device in accordance with claim 6 wherein said measuring of the sphericity of the corneal tissue is accomplished by measuring the eccentricity of the circularity of the superposed primary and rotated secondary images by a reticle having a scale for measurement of said eccentricity in dioptric units.

9. An optical device in accordance with claim 6 wherein said first beamsplitter means is disposed at an angle of 45° to the primary optical path.

10. An optical device in accordance with claim 6 wherein in said first mirror means is a full mirror of the first-surface type disposed parallel to said first beamsplitter means.

11. An optical device in accordance with claim 6 wherein said image rotating means is disposed along the axis of propagation of the secondary ray family and angularly displaced so as to rotate the secondary image 90° relative to the primary image.

12. An optical device in accordance with claim 6 wherein said second mirror is a full mirror of the first-surface type disposed parallel to said second beamsplitter means.

13. An optical device in accordance with claim 6 wherein said second beamsplitter is disposed at the intersection of the primary and secondary optical paths at an angle of 45° to the primary optical path.

14. An optical device in accordance with claim 6 wherein in said path lengthener means comprises four mirrors disposed at the corners of a rectangle whose dimensions are determined by the geometrical increase in path length needed to equalize the length of the primary and secondary optical paths, each pair of mirrors are parallel to each other, perpendicular to the other pair and disposed at an angle of 45° to the primary optical path.

15. An optical device in accordance with claim 14 wherein said path lengthener means provides an even number of reflective surfaces for deflecting the primary ray family so as to result in no left-to-right image reversal as viewed by the observer.

16. An optical device in accordance with claim 6 wherein said secondary image is obscured by an image occluding means for permitting the observer to distinguish between the primary image and the combined image.

17. An optical device in accordance with claim 16 wherein said occluding means interposes an opaque shutter for impeding the transmission of the secondary image.

18. An optical device in accordance with claim 16 wherein said occluding means provides an optical split field by modifying said second beamsplitter.

19. An optical device in accordance with claim 18 wherein said modification is providing a central opening in said second beamsplitter.

20. An optical device in accordance with claim 18 wherein said modification is halving said second beamsplitter.

21. An optical device in accordance with claim 16 wherein said occluding means mechanically rotates any of the beamsplitters or mirrors in the secondary optical path to deflect the secondary rays out of their normal path.

22. An optical device in accordance with claim 6 wherein a means for visually suppressing the intensity of the secondary image with respect to the intensity of the primary image is disposed in the secondary optical path so that the observer can visually distinguish the primary and secondary images.

23. An optical device in accordance with claim 22 wherein said means for visually suppressing the intensity of the secondary image is a spectrally neutral absorbing filter.

24. An optical device in accordance with claim 6 wherein a means for visually suppressing the intensity of the secondary image is a beamsplitter having an unequal reflectance-to-transmittance ratio, the reflectance value being smaller than the transmittance value.

25. An optical device in accordance with claim 6 wherein means for color coding the primary and secondary images is disposed in the respective optical paths so that the observer can visually distinguish the primary and secondary images.

26. An optical device in accordance with claim 25 wherein said means for color coding the primary and secondary images are colored light transmission filters.

27. An optical device in accordance with claim 25 wherein said means for color coding the primary and secondary images are dichroic beamsplitters.

28. An optical device in accordance with claim 25 wherein said means for color coding the primary and secondary images are dichroic beamsplitters in combination with colored light transmission filters.

29. An optical device in accordance with claim 6 wherein said optical device is be housed within a microscope ocular.

30. An optical device for measuring the sphericity of a surface whereby an abnormal condition can be detected and measured comprising a light source for illuminating a target which reflects image-forming rays which travel over a primary optical path, said image-forming rays being divided by a first beamsplitter means creating a primary ray family and a secondary ray family yielding a primary image and a secondary image respectively, said secondary ray family travelling along a secondary optical path and being rotated axially about its axis of propagation through a specifically defined angular displacement relative to the angular displacement of the primary ray family by an image rotating means, and said primary and secondary ray families being combined by a second beamsplitter means creating a combined superposed image formed from said primary image and said secondary image rotated relative to said primary image which may be visually compared and measured in order to determined sphericity of the surface.

31. An optical device in accordance with claim 30 wherein said image-forming rays reflected from the target form a circular image when reflected from a spherical surface and exhibit an eccentricity and form an elliptical image when reflected from a non-spherical surface, said target being the surface.

32. An optical device in accordance with claim 30 wherein said combined superposed image formed from said primary image and said secondary image rotated relative to said primary image is visually compared by a means for measuring the eccentricity of the circularity of the primary image with the rotated secondary image to determine sphericity of the surface.

33. An optical device in accordance with claim 30 wherein said measuring of the eccentricity of the circularity of the primary and secondary images is performed by a reticle in an ocular of an optical instrument, said reticle having a scale for measurement of said eccentricity in dioptric units.

34. An optical device in accordance with claim 30 wherein said optical device is housed within a microscope ocular.

* * * * *